United States Patent [19]

Steckel

[11] Patent Number: 5,464,416
[45] Date of Patent: Nov. 7, 1995

[54] LIGATING CLIP

[75] Inventor: Mark G. Steckel, Maineville, Ohio

[73] Assignee: Ethicon, Inc., Cincinnati, Ohio

[21] Appl. No.: 974,087

[22] Filed: Nov. 10, 1992

[51] Int. Cl.$^6$ .................................................. A61B 17/122
[52] U.S. Cl. ........................................................ 606/158
[58] Field of Search ...................................... 606/151, 157, 606/158, 142, 143, 139

[56] References Cited

U.S. PATENT DOCUMENTS

| | | | |
|---|---|---|---|
| 4,492,232 | 1/1985 | Green. | |
| 4,519,501 | 5/1985 | Cerwin | 206/339 |
| 4,527,562 | 7/1985 | Mericle. | |
| 4,612,923 | 9/1986 | Kronenthal. | |
| 4,616,651 | 10/1986 | Golden | 606/158 |
| 4,638,804 | 1/1987 | Jewusiak. | |
| 4,646,741 | 3/1987 | Smith. | |
| 5,062,846 | 11/1991 | Oh et al. | 606/158 |
| 5,160,339 | 11/1992 | Chen et al. | 606/158 |
| 5,171,249 | 12/1992 | Stefanchik et al. | 606/142 |

*Primary Examiner*—Tamara L. Graysay
*Attorney, Agent, or Firm*—Killworth, Gottman, Hagan & Schaeff

[57] ABSTRACT

A surgical fastener is provided which is adapted to be secured in a closed position about body tissue by a fastener-applying instrument. The surgical fastener comprises first and second leg members, each having distal and proximal ends. A resilient hinge connects the first and second leg members at their proximal ends. A latch mechanism is associated with the distal ends of the first and second leg members for locking the first and second leg members in a closed position about the body tissue. Lateral extensions are provided on the first and second leg members for engaging with the fastener-applying instrument to allow the instrument to move the first and second leg members toward one another until the latch mechanism locks the first and second leg members in a closed position about the body tissue. The first leg member and its associated lateral extensions and the second leg member and its associated lateral extensions may each define a substantially T-shaped, trapezoidal or bell-shaped cross section.

31 Claims, 5 Drawing Sheets

LIGATING CLIP

BACKGROUND OF THE INVENTION

The present invention relates generally to surgical fasteners and, more particularly, to a surgical ligating clip having laterally positioned engagement means for receiving a closing force from clip-applying jaws.

Surgical ligating clips have been used in the prior art to ligate blood vessels, ducts and other body tissue during surgery. Such clips have been produced from metals, such as titanium, tantalum and stainless steel. Clips made from polymeric materials are also known and may be preferable to metal clips in some surgical procedures. This is because polymeric clips do not disrupt post-operative diagnostic procedures, such as X-ray imaging, CAT scanning and the like. Further, when absorbable polymeric clips are employed, there is little likelihood of a long term foreign body reaction by the host in which the clips are implanted.

One example of a prior art polymeric clip is disclosed in U.S. Pat. No. 4,527,562, and comprises two leg members joined at their proximal ends by a hinge, with locking means provided at the distal ends of the leg members for securing same in a closed position. The clip further includes bosses provided on upper and lower outer surfaces of the top and bottom leg members, respectively, for mating with jaws of a clip-applying instrument. The clip is secured to body tissue by applying sufficient force via the clip-applying instrument to the upper and lower outer surfaces of the leg members to move them toward one another until the locking means locks the leg members in a closed position. This prior art ligating clip is commonly used in open surgical procedures.

For endoscopic applications, a ligating clip must be of a size which permits it to pass through a cannula passageway before being secured to body tissue. An additional limitation on its size is presented when the outer surfaces of its leg members are gripped by jaws of a clip-applying instrument. This results because the combined height of the clip and the jaws should not exceed the diameter of the cannula passageway. Exemplary of such a clip and applier is that disclosed in commonly assigned U.S. patent application Ser. No. 07/680,215, now U.S. Pat. No. 5,171,249, the disclosure of which is hereby incorporated by reference.

With polymeric clips, these size limitations may be problematic since the clips must be sufficiently stiff to ensure proper ligation of the attached tissue. Because the polymeric ligating clip in noted U.S. Pat. No. 4,527,562 is gripped on its upper and lower outer surfaces before being secured to body tissue, the clip dimensions are limited for endoscopic applications.

Accordingly, there is a need for a ligating clip and clip-applying instrument in which the clip-applying instrument grips the clip at locations other than on the upper and lower outer surfaces of the leg members of the clip.

SUMMARY OF THE PRESENT INVENTION

This need is met by the present invention wherein an improved ligating clip is provided which includes engagement means positioned laterally on its leg members for engagement with a clip-applying instrument. Due to the lateral location of the engagement means, the clip size can be maximized with respect to the diameter of a cannula so that the upper and lower outer surfaces of the top and bottom leg members, respectively, extend substantially completely across the diameter of the cannula passageway as the clip passes in a semi-closed state therethrough. Maximizing clip size allows the beam stiffness of the leg members to be increased. This, in turn, minimizes flexure or springback of the leg members when the clip is secured to body tissue.

In accordance with a first aspect of the present invention, a surgical fastener is provided which is adapted to be secured in a closed position about body tissue by a fastener-applying instrument. The surgical fastener comprises first and second leg members, each having distal and proximal ends. Resilient hinge means is provided for connecting the first and second leg members at their proximal ends. Latch means is associated with the distal ends of the first and second leg members for locking the first and second leg members in a closed position about the body tissue. Engagement means is positioned laterally on at least one of the first and second leg members for engaging with the fastener-applying instrument to allow the instrument to move the first and second leg members toward one another until the latch means locks the first and second leg members in a closed position about the body tissue.

Preferably, the engagement means comprises first and second lateral extensions integrally formed with the first leg member, and third and fourth lateral extensions integrally formed with the second leg member. In accordance with a first embodiment of the present invention, the first and second lateral extensions extend from opposing lateral faces of the first leg member and the third and fourth lateral extensions extend from opposing lateral faces of the second leg member. The first leg member and its associated lateral extensions and the second leg member and its associated lateral extensions each define a substantially T-shaped cross section.

In accordance with a second embodiment of the present invention, the first leg member and its associated lateral extensions and the second leg member and its associated lateral extensions each define a substantially trapezoidal cross section. According to a third embodiment, the first leg member and its associated lateral extensions and the second leg member and its associated lateral extensions each define a substantially bell-shaped cross section.

In accordance with a second aspect of the present invention, a combination is provided comprising a clip-applying instrument and a ligating clip which is adapted to be secured in a closed position about body tissue by the clip-applying instrument. Preferably, the clip is configured in the same manner as the clip discussed above with respect to the first aspect of the present invention.

In accordance with a third aspect of the present invention, a method is provided for securing a ligating clip in a closed position about body tissue. The ligating clip comprises first and second leg members having distal and proximal ends, hinge means for connecting the first and second leg members at their proximal ends, latch means associated with the distal ends of the first and second leg members for locking the first and second leg members in a closed position, and engagement means, positioned laterally on at least one of the first and second leg members, for engaging with a fastener-applying instrument. The method comprises the steps of: engaging the laterally positioned engagement means with the fastener-applying instrument; positioning the clip such that the leg members extend on opposite sides of the body tissue; and employing the fastener-applying instrument to move the first and second leg members toward one another until the latch means locks the first and second leg members in a closed position with the body tissue engaged therebetween.

Preferably, the method further comprises the step of passing the clip through the passageway of a cannula prior to performing the step of positioning the clip such that the leg members extend on opposite sides of the body tissue.

The fastener-applying instrument may move the first and second leg members toward one another by applying a closing force to either the engagement means or upper and lower outer surfaces of the first and second leg members.

Accordingly, it is an object of the present invention to provide an improved surgical fastener which includes engagement means positioned laterally on at least one of its leg members for engaging with a fastener-applying instrument. It is another object of the present invention to provide an improved sterile ligating clip which includes lateral extensions provided on its leg members for engaging with a clip-applying instrument. It is a further object of the present invention to provide an improved ligating clip having engagement means positioned laterally thereon so as to allow maximum use of a cannula passageway during endoscopic applications. It is yet another object of the present invention to provide a clip-applying instrument for engaging with lateral extensions on a ligating clip and applying a closing force to either the lateral extensions or the upper and lower outer surfaces of the clip. These and other objects and advantages of the present invention will be apparent from the following description, the accompanying drawings and the appended claims.

DETAILED DESCRIPTION OF THE PREFERRED EMBODIMENTS

Figure 1:
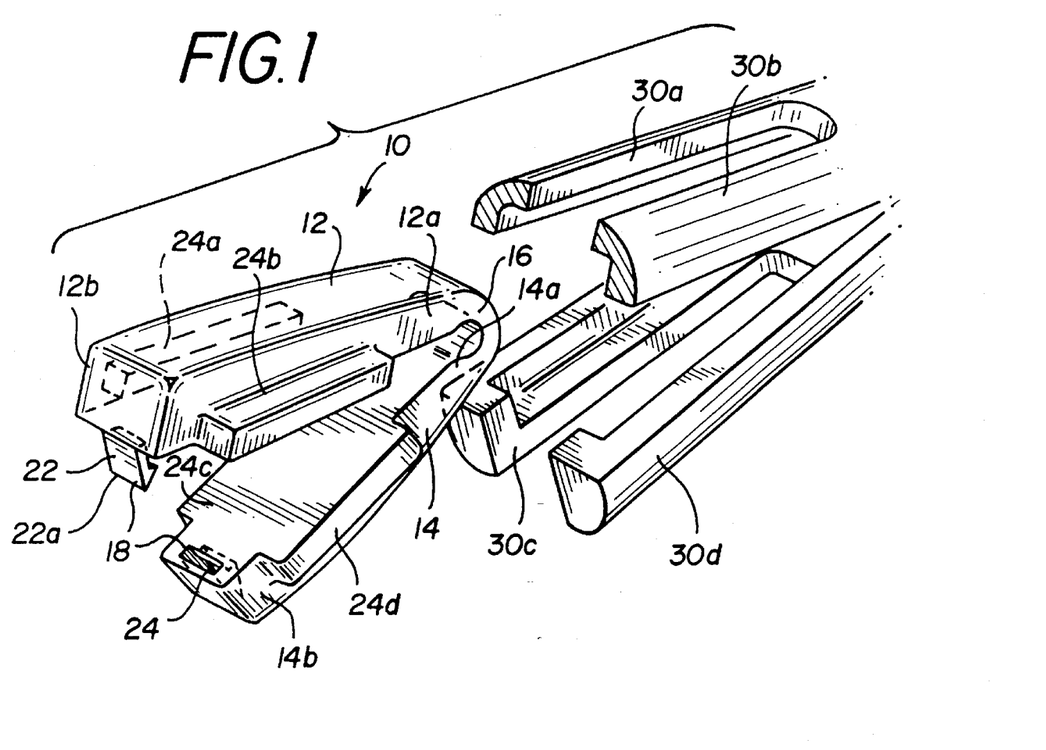
FIG. 1 is a perspective view of a ligating clip and jaws of a clip-applying instrument, each constructed in accordance with a first embodiment of the present invention, with the upper jaws shown partially broken away.

Reference is now made to FIG. 1, which illustrates a ligating clip 10 formed in accordance with a first embodiment of the present invention. The ligating clip 10 includes first and second leg members 12 and 14 connected at their proximal ends 12a and 14a by a resilient hinge section 16. Provided at the distal ends 12b and 14b of the first and second leg members 12 and 14 is latch means 18 for locking the leg members 12 and 14 in a closed position about body tissue, such as a vessel 20, shown in FIG. 2. In the illustrated embodiment, the latch means 18 comprises a hook member 22 which is adapted to be lockingly received within a recess 24 located in the distal end 14b of the second leg member 14. The hook member 22 is provided with a sharp edge 22a for penetrating any connecting tissue (not shown) which might surround the vessel 20.

Figure 2:
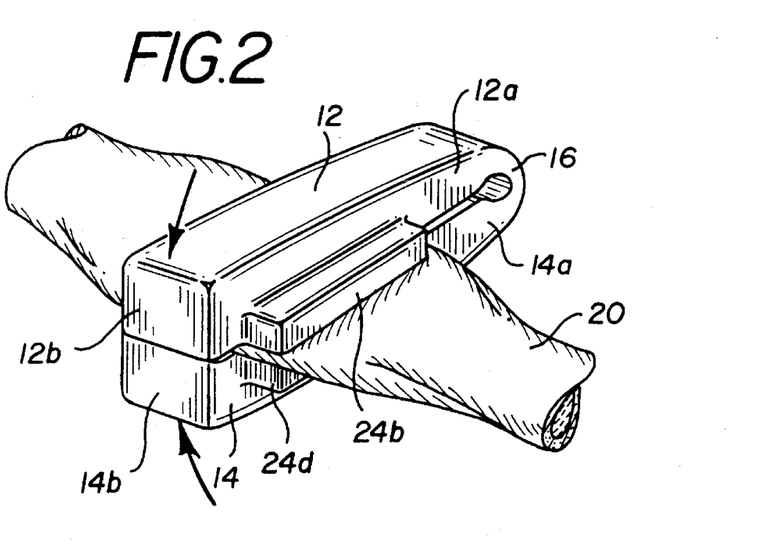
FIG. 2 is a perspective view of the clip of FIG. 1 shown secured to a vessel.

First and second lateral extensions 24a and 24b are integrally formed with the first leg member 12, and third and fourth lateral extensions 24c and 24d are integrally formed with the second leg member 14. The lateral extensions 24a–24d extend outwardly from opposing side walls of the leg members 12 and 14 and are adapted to receive a clip closing force. The force applied to lateral extensions 24a–24d cause the distal ends 12b and 14b of the leg members 12 and 14 to move toward one another until the latch means 18 locks them in a closed position, with the vessel 20 engaged therebetween as shown in FIG. 2.

Figure 3:
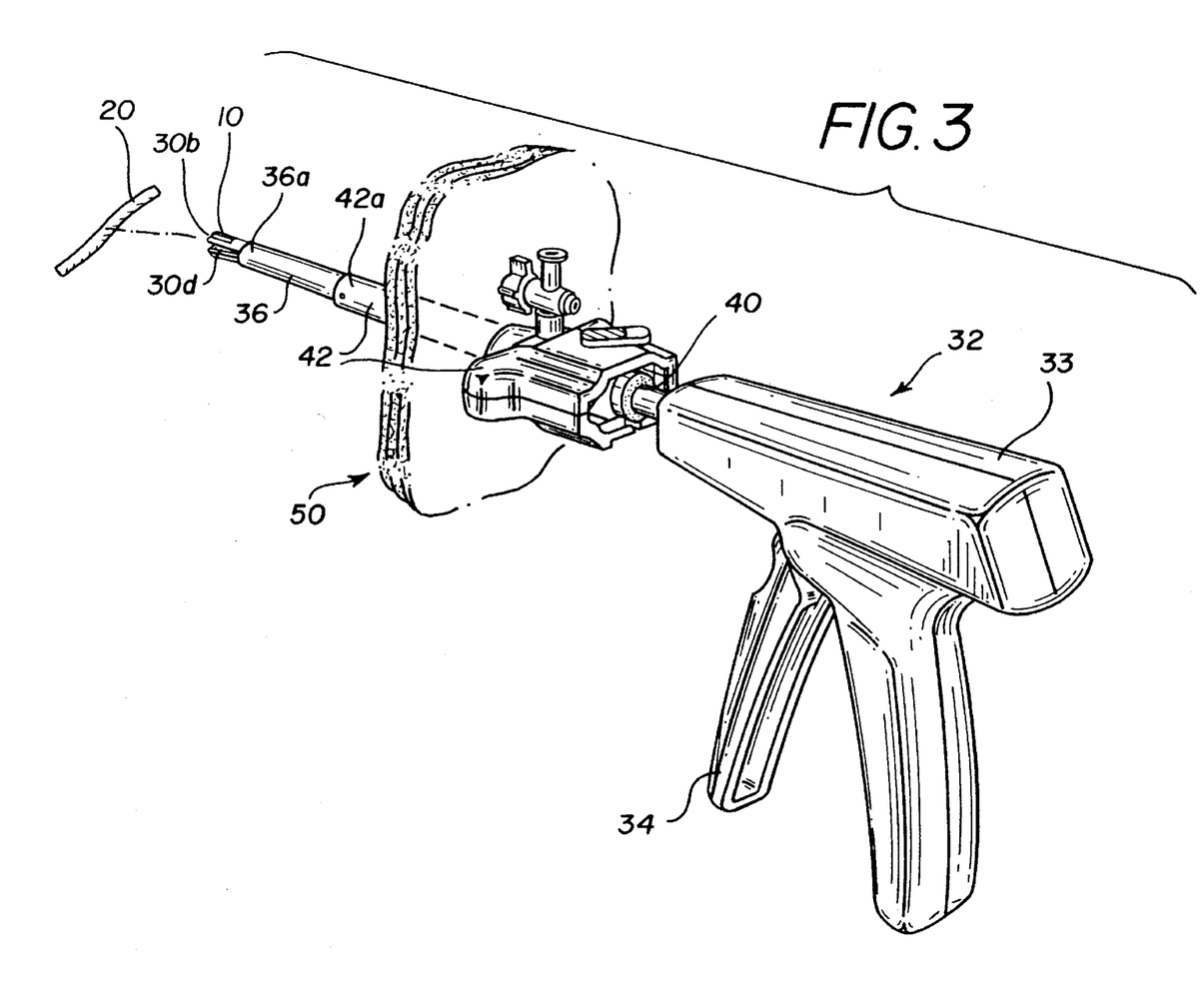
FIG. 3 is a perspective view of a clip-applying instrument and a cannula with the cylindrical tubular extension of the instrument inserted through the passageway of the cannula for use during an endoscopic procedure.

It will be understood by those skilled in the art that a variety of clip-applying instruments can be used for securing the ligating clip 10 to body tissue. One example of such a clip-applying instrument 32 is shown in FIG. 3. The instrument 32 includes jaws 30a–30d, which are more clearly shown in FIGS. 1, 4 and 5, a housing 33, a pivotable trigger 34, and a cylindrical tubular extension 36. A suitable actuating mechanism (not shown) extends through the housing 33 and the tubular extension 36 and connects with the jaws 30a–30d at its distal end and with the trigger 34 at its proximal end. Opening and closing of the jaws 30a–30d is effected by a surgeon through actuation of the trigger 34.

Figure 4:
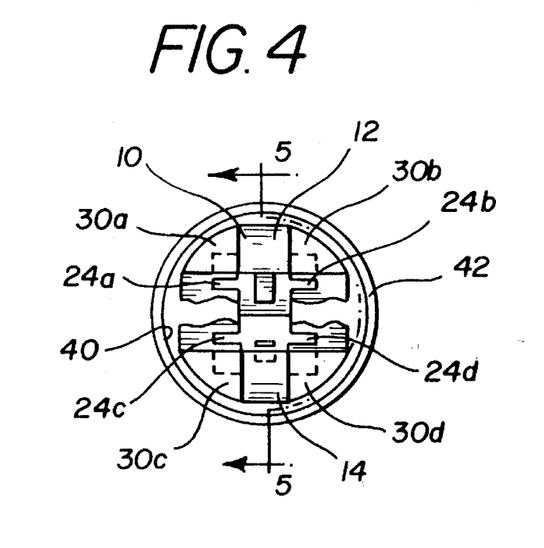
FIG. 4 is a distal end view of the cannula of FIG. 3 with the jaws of the clip-applying instrument gripping the clip of FIG. 1 within the cannula passageway.
Figure 5:
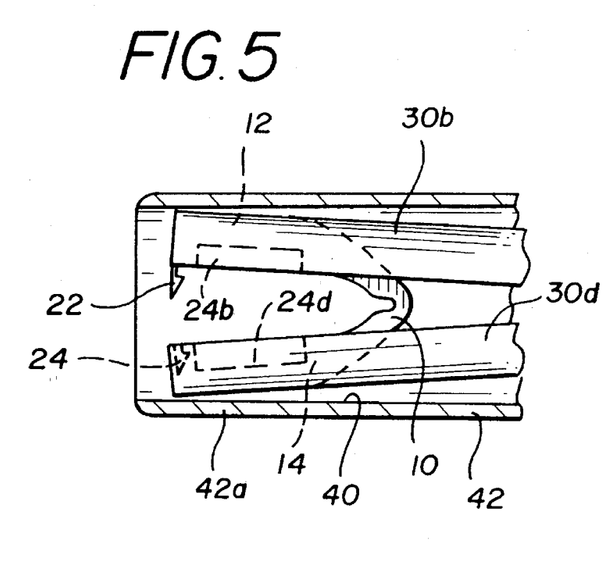
FIG. 5 is a view taken along section line 5—5 in FIG. 4.

For use during an endoscopic procedure, the clip 10 is held between the jaws 30a–30d, adjacent to the distal end 36a of the tubular extension 36, and is inserted through a passageway 40 of a cannula 42, as shown in FIG. 3. The cannula has previously been inserted through tissue 50 in a known manner. The clip 10 passes through the cannula passageway 40 in a partially closed state, as shown in FIGS. 4 and 5. After the jaws 30a–30d and the clip 10 have passed beyond the distal end 42a of the cannula 42, the jaws 30a–30d separate to allow the clip 10 to expand to its substantially fully opened state. By manipulating the clip-applying instrument 32, a surgeon positions the clip 10 so that its leg members 12 and 14 extend on opposite sides of the vessel 20 or other body tissue to be ligated. The trigger 34 is then actuated by the surgeon, causing the jaws 30a–30d to apply a force to the lateral extensions 24a–24d. This moves the leg members 12 and 14 toward one another until the latch means 18 locks the leg members 12 and 14 in a closed position, with the vessel 20 engaged therebetween.

Figures 6, 7:
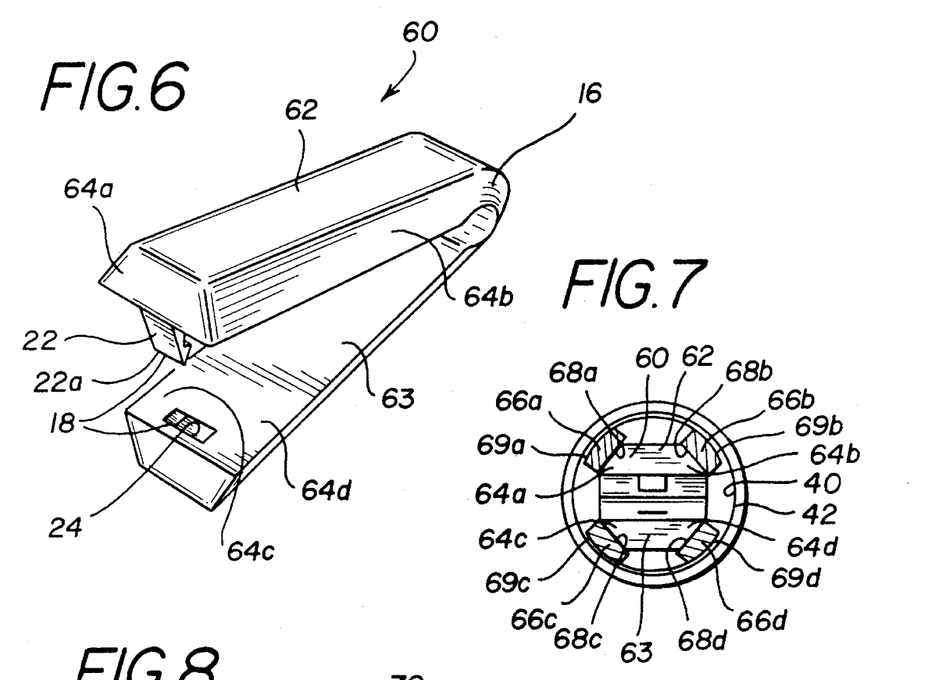
FIG. 6 is a perspective view of a ligating clip formed in accordance with a second embodiment of the present invention.
FIG. 7 is a distal end view of a cannula having jaws gripping the clip of FIG. 6 within the cannula passageway.

A ligating clip 60, configured in accordance with a second embodiment of the present invention, is shown in FIGS. 6 and 7, where like reference numerals indicate like elements. In this embodiment, the clip 60 includes a first leg member 62 which is integrally formed with first and second lateral extensions 64a and 64b. Together, the lateral extensions 64a and 64b and the first leg member 62 define a substantially trapezoidal cross section. The clip 60 further includes a second leg member 63 which is integrally formed with third and fourth lateral extensions 64c and 64d. The lateral extensions 64c and 64d and the second leg member 63 also define a substantially trapezoidal cross section.

In accordance with the second embodiment of the present invention, the clip-applying instrument is provided with jaws 66a–66d having substantially planar inner surfaces 68a–68d for engaging the lateral extensions 64a–64d of the ligating clip 60, see FIG. 7. The outer surfaces 69a-69d of the jaws 66a–66d are curved to allow easy passage through, and full use of, the circular cannula passageway 40.

Figures 8, 9:
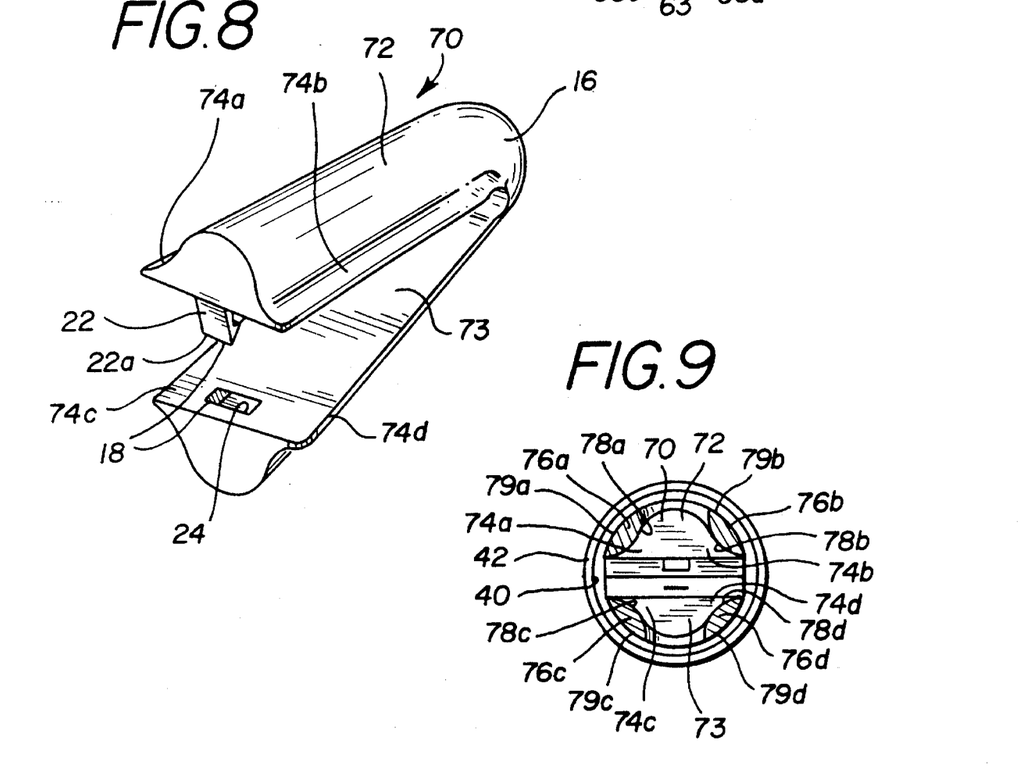
FIG. 8 is a perspective view of a ligating clip formed in accordance with a third embodiment of the present invention.
FIG. 9 is a distal end view of a cannula having jaws gripping the clip of FIG. 8 within the cannula passageway.

A ligating clip 70, formed in accordance with a third embodiment of the present invention, is shown in FIGS. 8 and 9, where like elements are referenced by like numerals. In this embodiment, the clip 70 includes a first leg member 72 and integrally formed first and second lateral extensions 74a and 74b. Together, the first leg member 72 and the lateral extensions 74a and 74b define a substantially bell-shaped cross section. The clip 70 further includes a second leg member 73 and integrally formed third and fourth lateral extensions 74c and 74d. Together, the second leg member 73 and the lateral extensions 74c and 74d also define a bell-shaped cross section.

In accordance with the third embodiment of the present invention, the clip-applying instrument is provided with jaws 76a–76d having curved inner surfaces 78a–78d conforming to the curved lateral extensions 74a–74d for secure engagement with same, see FIG. 9. The outer surfaces 79a–79d of the jaws 76a–76d are curved to allow easy passage through and full use of the circular cannula passageway 40.

Figure 10:
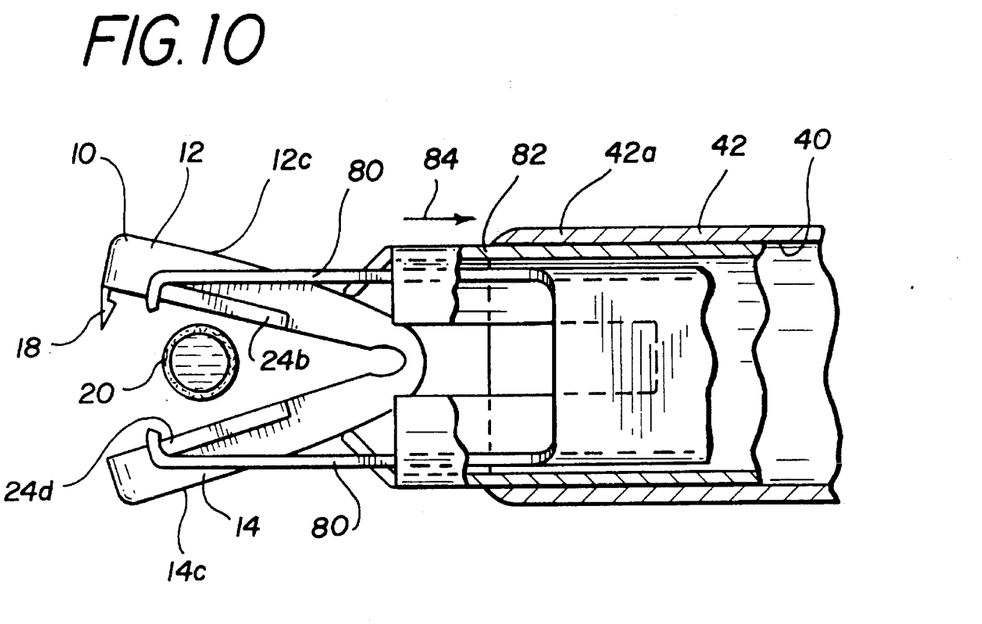
FIG. 10 is a side view, partially in section, showing an alternative embodiment of a clip-applying instrument including gripping arms and a camming element supporting the clip of FIG. 1 before acting to close the clip about a vessel.
Figure 11:
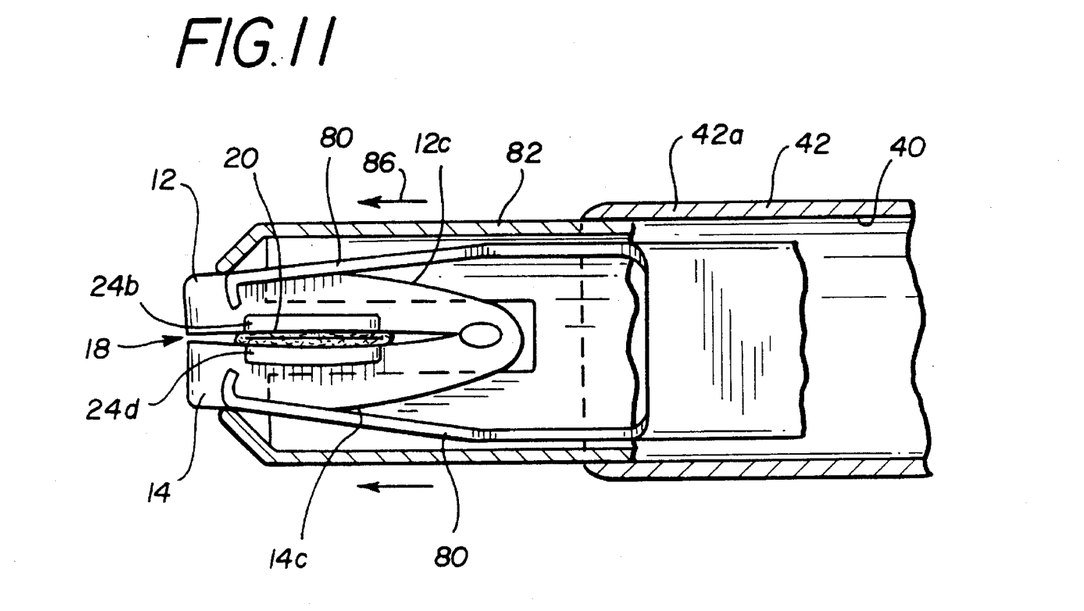
FIG. 11 is a side view, partially in section, illustrating the movement of the camming element relative to the gripping arms of the clip-applying instrument of FIG. 10 for closing the clip about the vessel.

An alternative embodiment of the clip-applying instrument of the present invention is shown in FIGS. 10 and 11. In this embodiment, the clip-applying apparatus comprises four gripping arms 80, only two of which are shown, and a reciprocating camming element 82. The gripping arms 80 engage with the lateral extensions 24a–24d of the ligating clip 10 of FIGS. 1 and 2 and act with the camming element 82 to hold the clip 10 in a partially closed state as the clip 10 passes through the cannula passageway 40. After passing beyond the distal end 42a of the cannula 42, the camming element 82 is moved in a direction, denoted by arrow 84 in FIG. 10, away from the clip 10 to allow the clip 10 to expand to its substantially fully opened position. With the clip 10 thus expanded, it is positioned so that its leg members 12 and 14 are on opposite sides of the vessel 20 or other tissue to be ligated. The camming element 82 is then moved in a direction, denoted by arrow 86 in FIG. 11, toward the clip 10 to apply a force against upper and lower outer surfaces 12c and 14c of the leg members 12 and 14. Leg members 12 and 14 are moved toward one another until the locking means 18 locks the leg members 12 and 14 in a closed position so as to close off the lumen of the vessel 20.

Following securement of the clip 10 to the vessel 20, the camming element 82 is moved away from the clip 10. The camming element 82 and the gripping arms 80 are then withdrawn from the cannula 42.

The ligating clips of the present invention may be molded from a biologically acceptable polymeric material which may be absorbable or non-absorbable. Preferred absorbable polymers include poly(p-dioxanone), polyglycolide, polylactide, polycaprolactone, polyhydroxybutyrate, polyhydroxyvalerate, polyanhydrides, and copolymers thereof. Preferred non-absorbable polymers include nylon, polyester and polypropylene. The clips may also be cast or machined from solid polymeric materials. The clips may also be formed of other suitable materials such as a metal.

As will be appreciated by those skilled in the art, the ligating clips of the present invention may be used in open surgical procedures. The aforementioned clip-applying instruments or like apparatus may be employed for securing the clips to body tissue during such procedures.

It is further contemplated by the present invention that the first leg member and its associated lateral extensions and the second leg member and its associated lateral extensions may form other shapes in cross section in addition to those which are illustrated with regard to the previously noted embodiments of the present invention. Additionally, the lateral extensions on the first and second leg members may be positioned so that they do not increase the area of the clip that engages body tissue.

It is also contemplated that a clip-applying instrument, preloaded with a plurality of ligating clips of the present invention, may be employed for feeding the ligating clips successively to a securement position and for subsequently securing each clip to body tissue as each clip is moved to that position.

Having described the invention in detail and by reference to preferred embodiments thereof, it will be apparent that modifications and variations are possible without departing from the scope of the invention defined in the appended claims.

What is claimed is:

1. A surgical fastener adapted to be secured in a closed position about body tissue by a fastener-applying instrument comprising:

first and second leg members each having distal and proximal ends and an inner tissue engaging surface and an opposing outer surface;

resilient hinge means for connecting said first and second leg members at their proximal ends; and engagement means, positioned laterally on at least one of said first and second leg members between said inner and outer surfaces of said one leg member without extending beyond said opposing outer surface of said one leg member, for engaging with said fastener-applying instrument to allow said instrument to move said first and second leg members toward one another until said first and second leg members are in a closed position about said body tissue.

2. A surgical fastener as set forth in claim 1, wherein said engagement means is positioned laterally on both said first and second leg members.

3. A surgical fastener as set forth in claim 1, wherein said engagement means comprises first and second lateral extensions integrally formed with said first leg member and third and fourth lateral extensions integrally formed with said second leg member.

4. A surgical fastener as set forth in claim 3, wherein said first and second lateral extensions extend from opposing lateral faces of said first leg member and said third and fourth lateral extensions extend from opposing lateral faces of said second leg member.

5. A surgical fastener as set forth in claim 4, wherein said first leg member and its associated lateral extensions and said second leg member and its associated lateral extensions each define a substantially T-shaped cross section.

6. A surgical fastener as set forth in claim 3, wherein said first leg member and its associated lateral extensions and said second leg member and its associated lateral extensions, each define a substantially trapezoidal cross section.

7. A surgical fastener as set forth in claim 3, wherein said first leg member and its associated lateral extensions and said second leg member and its associated lateral extensions each define a substantially bell-shaped cross section.

8. A surgical fastener as set forth in claim 1, wherein said first and second leg members and said resilient hinge means are made from a polymeric material.

9. A surgical fastener as set forth in claim 1, wherein said first and second leg members and said resilient hinge means are made from an absorbable polymeric material.

10. A combination comprising a clip-applying instrument and a ligating clip adapted to be secured in a closed position about body tissue by said clip-applying instrument, said ligating clip comprising:

first and second leg members each having distal and proximal ends and an inner tissue engaging surface and an opposing outer surface;

resilient hinge means for connecting said first and second leg members at their proximal ends;

latch means associated with the distal ends of said first and second leg members for locking said first and second leg members in a closed position about said body tissue; and engagement means, positioned laterally on at least one of said first and second leg members between said inner and outer surfaces of said one leg member without extending beyond said opposing outer surface of said one leg member, for engaging with said clip-applying instrument to allow said instrument to move said first and second leg members toward one another until said latch means locks said first and second leg members in a closed position about said body tissue.

11. The combination as set forth in claim 10, wherein said engagement means is positioned laterally on both said first and second leg members.

12. The combination as set forth in claim 10, wherein said engagement means comprises first and second lateral extensions integrally formed with said first leg member and third and fourth lateral extensions integrally formed with said second leg member.

13. The combination as set forth in claim 12, wherein said first and second lateral extensions extend from opposing lateral faces of said first leg member and said third and fourth lateral extensions extend from opposing lateral faces of said second leg member.

14. The combination as set forth in claim 13, wherein said first leg member and its associated lateral extensions and said second leg member and its associated lateral extensions each define a substantially T-shaped cross section.

15. The combination as set forth in claim 12, wherein said first leg member and its associated lateral extensions and said second leg member and its associated lateral extensions each define a substantially trapezoidal cross section.

16. The combination as set forth in claim 12, wherein said first leg member and its associated lateral extensions and said second leg member and its associated lateral extensions each define a substantially bell-shaped cross section.

17. The combination as set forth in claim 10, wherein said first and second leg members, said resilient hinge means and said latch means are made from a polymeric material.

18. The combination as set forth in claim 10, wherein said first and second leg members, said resilient hinge means and said latch means are made from an absorbable polymeric material.

19. A method for securing a ligating clip in a closed position about body tissue, wherein said ligating clip comprises first and second leg members having distal and proximal ends and an inner tissue engaging surface and an opposing outer surface, hinge means for connecting said first and second leg members at their proximal ends, latch means associated with the distal ends of said first and second leg members for locking said first and second leg members in a closed position, and engagement means, positioned laterally on at least one of said first and second leg members between said inner and outer surfaces of said one leg member without extending beyond said opposing outer surface of said one leg member, for engaging with a fastener-applying instrument, said method comprising the steps of:

engaging said laterally positioned engagement means with said fastener-applying instrument;

positioning said clip such that said leg members extend on opposite sides of said body tissue; and employing said fastener-applying instrument to move said first and second leg members toward one another until said latch means locks said first and second leg members in a closed position with said body tissue engaged therebetween.

20. A method for securing a ligating clip in a closed position about body tissue as set forth in claim 19, further comprising the step of passing said clip through the passageway of a cannula prior to performing the step of positioning said clip such that said leg members extend on opposite sides of said body tissue.

21. A method for securing a ligating clip in a closed position about body tissue as set forth in claim 19, wherein said fastener-applying instrument moves said first and second leg members toward one another by applying a closing force to said engagement means.

22. A method for securing a ligating clip in a closed position about body tissue as set forth in claim 19, wherein said fastener-applying instrument moves said first and second leg members toward one another by applying a closing force to respective outer surfaces of said first and second leg members.

23. A surgical fastener adapted to be secured in a closed position about body tissue by a fastener-applying instrument comprising:

first and second leg members each having distal and proximal ends and an inner tissue engaging surface and an opposing outer surface;

resilient hinge means for connecting said first and second leg members at their proximal ends;

latch means associated with the distal ends of said first and second leg members for locking said first and second leg members in a closed position about said body tissue; and engagement means, positioned laterally on at least one of said first and second leg members between said inner and outer surfaces of said one leg member without extending beyond said opposing outer surface of said one leg member, for engaging with said fastener-applying instrument to allow said instrument to move said first and second leg members toward one another until said latch means locks said first and second leg members in a closed position about said body tissue.

24. A surgical fastener as set forth in claim 23, wherein said engagement means is positioned laterally on both said first and second leg members.

25. A surgical fastener as set forth in claim 23, wherein said engagement means comprises first and second lateral extensions integrally formed with said first leg member and third and fourth lateral extensions integrally formed with said second leg member.

26. A surgical fastener as set forth in claim 25, wherein said first and second lateral extensions extend from opposing lateral faces of said first leg member and said third and fourth lateral extensions extend from opposing lateral faces of said second leg member.

27. A surgical fastener as set forth in claim 26, wherein said first leg member and its associated lateral extensions and said second leg member and its associated lateral extensions each define a substantially T-shaped cross section.

28. A surgical fastener as set forth in claim 25, wherein said first leg member and its associated lateral extensions and said second leg member and its associated lateral extensions each define a substantially trapezoidal cross section.

29. A surgical fastener as set forth in claim 25, wherein said first leg member and its associated lateral extensions and said second leg member and its associated lateral extensions each define a substantially bell-shaped cross section.

30. A surgical fastener as set forth in claim 23, wherein said first and second leg members, said resilient hinge means and said latch means are made from a polymeric material.

31. A surgical fastener as set forth in claim 23, wherein said first and second leg members, said resilient hinge means and said latch means are made from an absorbable polymeric material.

* * * * *